United States Patent
Claussner et al.

Patent Number: 5,081,113
Date of Patent: Jan. 14, 1992

[54] NOVEL 3-KETO-STEROIDS

[75] Inventors: André Claussner, Villemomble; Jacques Leclaire, Massy; Lucien Nedelec, Le Raincy; Daniel Philibert, La Varenne Saint Hilaire, all of France

[73] Assignee: Roussel Uclaf, Paris, France

[21] Appl. No.: 497,564

[22] Filed: Mar. 21, 1990

[30] Foreign Application Priority Data

Mar. 22, 1989 [FR] France ................ 89 03741

[51] Int. Cl.$^5$ .................. C07J 43/00; C07J 7/00; A61K 31/565
[52] U.S. Cl. .................. 514/176; 540/109; 544/295; 552/622; 552/639
[58] Field of Search ................ 514/177, 176; 540/109; 544/294, 295; 552/622, 639

[56] References Cited

U.S. PATENT DOCUMENTS 4,076,737 2/1978 Anner et al. ............. 540/109

FOREIGN PATENT DOCUMENTS 263213 4/1988 European Pat. Off.

OTHER PUBLICATIONS

Jacobsen, I. Med. Chem 1990, 33 1145-1151.

Primary Examiner—Mukund J. Shah
Assistant Examiner—E. C. Ward
Attorney, Agent, or Firm—Bierman and Muserlian

[57] ABSTRACT

A compound selected from the group consisting of a compound of the formula

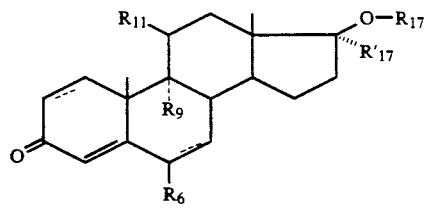

wherein $R_6$ is selected from the group consisting of halogen, —$CH_3$, fluorine and chlorine, $R_9$ and $R_{11}$ together form a second bond at 9(11) or $R_9$ is hydrogen or fluorine and $R_{11}$ is selected from the group consisnting of hydrogen, —OH and =O, the dotted lines in rings A and B indicate a possible additonal bond at 1(2) and 6(7), $R_{17}$ is hydrogen or acyl or an organic carboxylic acid of 1 to 18 carbon atoms, $R'_{17}$ is

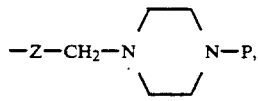

Z is selected from the group consisting of a single bond, alkylene of 1 to 5 carbon atoms and alkenylene and alkynylene of 2 to 5 carbon atoms, P is pyrimidinyl or pyridyl optionally substituted with one or two individual members of the group consisting of —$NH_2$, alkylamino, dialkylamino and aminated 5- or 6- membered heterocycles optionally substituted with alkyl of 1 to 3 carbon atoms and its non-toxic, pharmaceutically acceptable acid addition salts having anti-inflammatory and anti-oxidation activity.

35 Claims, No Drawings

NOVEL 3-KETO-STEROIDS

STATE OF THE ART

Related prior art includes PCT applications No. WO.A. 87/01,706 and WO.A.87/07,895 and U.S. Pat. No. 3,483,233.

OBJECTS OF THE INVENTION

It is an object of the invention to provide the novel compounds of formula I and their non-toxic, pharmaceutically acceptable acid addition salts and a novel process and novel intermediates for their preparation.

It is another object of the invention to provide novel anti-inflammatory compositions and a method of treating inflammation in warm-blooded animals.

These and other objects and advantages of the invention will become obvious from the following detailed description.

THE INVENTION

The novel compounds of the invention are selected from the group consisting of a compound of the formula

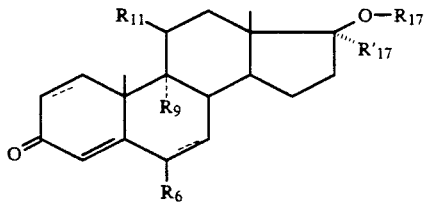

I wherein $R_6$ is selected from the group consisting of halogen, —$CH_3$, fluorine and chlorine, $R_9$ and $R_{11}$ together form a second bond at 9(11) or $R_9$ is hydrogen or fluorine and $R_{11}$ is selected from the group consisting of hydrogen, —OH and =O, the dotted lines in rings A and B indicate a possible additional bond at 1(2) and 6(7), $R_{17}$ is hydrogen or acyl of an organic carboxylic acid of 1 to 18 carbon atoms, $R'_{17}$ is

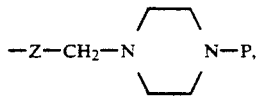

Z is selected from the group consisting of a single bond, alkylene of 1 to 5 carbon atoms and alkenylene and alkynylene of 2 to 5 carbon atoms, P is pyrimidinyl or pyridyl optionally substituted with one or two individual members of the group consisting of —$NH_2$, alkylamino, dialkylamino and aminated 5- or 6-membered heterocycles optionally substituted with alkyl of 1 to 3 carbon atoms and its non-toxic, pharmaceutically acceptable acid addition salts.

When $R_{17}$ is acyl, the latter can be the derivative of a saturated or unsaturated aliphatic or cycloaliphatic carboxylic acid and particularly of an alkanoic acid such as acetic acid, propionic acid, butyric acid or isobutyric acid, valeric acid or undecylic acid, of a hydroxyalkanoic acid such as, for example, hydroxyacetic acid, of a cycloalkanecarboxylic or (cycloalkyl)alkanoic acid such as cyclopropanecarboxylic acid, cyclopentanecarboxylic acid or cyclohexanecarboxylic acid, cyclopentylacetic acid, or cyclohexylacetic acid or propionic acid, of benzoic acid or phenylalkanoic acid such as phenylacetic or phenylpropionic acid, of an amino acid such as diethyl aminoacetic acid or aspartic acid or of formic acid. It is preferably the derivative of acetic acid.

In $R'_{17}$, when Z is alkylene, the latter is preferably methylene, ethylene or trimethylene. When Z is alkenylene, the latter is preferably vinylene and when Z is an alkynylene, the latter is preferably ethynylene. When P is substituted with an alkylamino, the alkyl preferably has 1 to 4 carbon atoms such as methyl, ethyl, n-propyl, isopropyl, n-butyl, isobutyl, and tert-butylamino with methylamino or ethylamino being preferred. When P is substituted with dialkylamino, the alkyls have 1 to 4 carbon atoms such as dimethyl, diethyl or methylethylamino. When P is substituted with one or two aminated heterocycles, the latter can be a saturated heterocycle, preferably pyrrolidine or piperidine optionally substituted with alkyl such as methyl, ethyl, propyl or isopropyl, preferably methyl or ethyl, or an unsaturated heterocycle, preferably pyrrole optionally substituted with alkyl such as methyl.

Examples of suitable acids for the formation of the non-toxic, pharmaceutically acceptable acid addition salts of the compounds of formula I are inorganic acids such as hydrochloric acid, hydrobromic acid, nitric acid, sulfuric acid phosphoric acid, organic acids such as acetic acid, formic acid, propionic acid, maleic acid, fumaric acid, succinic acid, tartaric acid, citric acid, oxalic acid, glyoxylic acid and aspartic acid; alkanesulfonic acids such as methanesulfonic acid or ethanesulfonic acid; arylsulfonic acids such as benzenesulfonic acid or p-toluenesulfonic acid and arylcarboxylic acids such as benzoic acid.

Among the preferred compounds of formula I are those wherein P is pyrimidinyl or pyridyl substituted with 2 identical or different dialkylamino or aminated 5- or 6-membered heterocycles, especially 2,6-bis(1-pyrrolidinyl)-4-pyrimidinyl, 5,6-bis(diethylamino)-2-pyridyl, or 3,6-bis(diethylamino)-2-pyridyl, those wherein R is hydrogen or methyl, those wherein the 6(7) dotted line is a second bond, those wherein $R_9$ is hydrogen and $R_{11}$ is —OH, those wherein the 1(2)-dotted line indicates a second bond, those where $R_{17}$ is hydrogen and those wherein $R'_{17}$ is

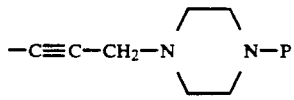

Specific preferred compounds of formula I are 17α-[3-{4-[2,6-bis(1-pyrrolidinyl)-4-pyrimidinyl]-1-piperazinyl}-1-propynyl]-Δ$^{4,6}$-androstadien-11β,17β-diol-3-one, 17α-[3-{4-[2,6-bis(1-pyrrolidinyl)-4-pyrimidinyl]-1-piperazinyl}-1-propynyl]-6-methyl-Δ$^{1,4,6}$-androstatrien-11β,17β-diol-3-one, 17α-[3-{4-[5,6-bis(diethylamino)-2-pyridyl]-1-piperazinyl}-1-propynyl]-6-methyl-Δ$^{1,4,6}$-androstatrien-11β,17β-diol-3-one, 17α-[3-{4-[3,6-bis(diethylamino)-2-pyridyl]-1-piperazinyl}-1-propynyl]-6-methyl-Δ$^{1,4,6}$-androstatrien-11β,17β-diol-3-one, and their salts.

The novel process of the invention for the preparation of the compounds of formula I comprises reacting a compound of the formula

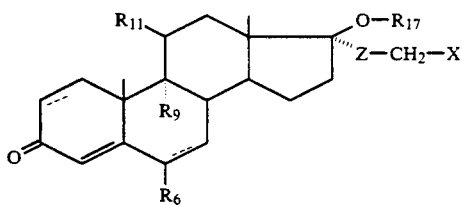
II wherein X is halogen and $R_6$, $R_9$, $R_{11}$, the dotted lines, $R_{17}$ and Z have the above meaning with a compound of the formula

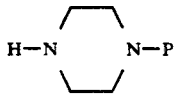
III wherein P has the above meaning in a neutral solvent and in the presence of a base to form a compound of formula I and, if desired, reacted with an acid to obtain the corresponding acid addition salt.

The compounds of formula I are obtained using a compound of formula II in which X is chlorine, bromine or iodine working in a neutral solvent such as dimethylformamide, tetrahydrofuran, methylene chloride, acetonitrile, ethyl ether or acetone in the presence of a base such as an alkali metal carbonate or bicarbonate, preferably sodium or potassium carbonate or bicarbonate, triethylamine or diisopropylethylamine.

In a preferred embodiment of the process of the invention, the compound of formula II is either 17α-(3-bromo-1-propynyl)-$\Delta^{4,6}$-androstadien-11β,17β-diol-3-one or 17α-(3-bromo-1-propynyl)-6-methyl-$\Delta^{1,4,6}$-androstatrien-11β,17β-diol-3-one, the neutral solvent is acetone, the base is potassium carbonate and the compound of formula III is either 2,4-bis(1-pyrrolidinyl)-6-(1-piperazinyl)-pyrimidine:

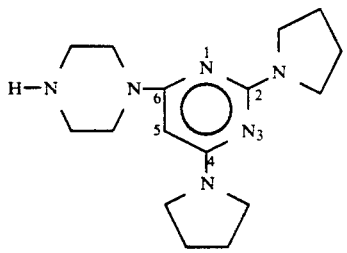

which may be obtained according to the preparation described in Patent Application No. WO 87/01,706 or N,N,N',N'-tetraethyl-6-(1-piperazinyl)-2,3-pyridinediamine:

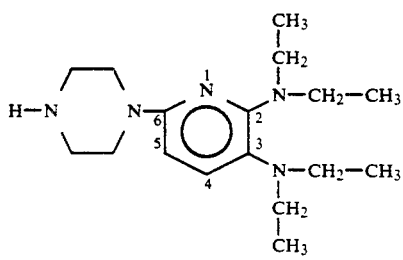

which, although named erroneously, may be obtained according to the preparation described in Patent Application No. WO 87/01,706 or N,N,N',N'-tetraethyl-6-(1-piperazinyl)-2,5-pyridinediamine:

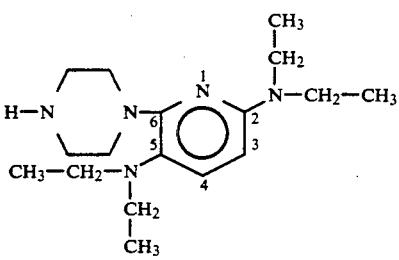

described in French Patent application No. 89-03740, the preparation of which is given later in the experimental part and which, contrary to what is stated, cannot be obtained according to the preparation in Patent Application No. WO 87/01,706.

The novel anti-inflammatory compositions of the invention are comprised of an anti-inflammatorily effective amount of at least one compound of formula I and its non-toxic, pharmaceutically acceptable acid addition salts and an inert pharmaceutical carrier. The compositions may be in the form of tablets, dragees, capsules, pomades, creams and injectable solutions or suspensions.

Examples of suitable excipients are talc, starch, aqueous or non-aqueous vehicles, fats of animal or vegetable origin, paraffin derivatives, glycols, the various wetting, dispersant or emulsifying agents and preservatives. The salts of the products of formula I which are more water-soluble are preferably used for aqueous formulations intended for intravenous injection.

The compositions can be used in the treatment of inflammatory reactions; they are advantageous for the treatment of local inflammatory reactions such as, for example, oedema, dermatoses, pruritus, the various forms of eczema and solar erythema or for the treatment of acute inflammatory diseases or chronic inflammatory diseases, for example rheumatoid arthritis, psoriasis or multiple sclerosis. They also display an advantageous anti-inflammatory activity, for example in the phenomena of acute inflammation mediated by arachidonic acid derivatives.

The compositions of the invention also display advantageous antioxidant activity by inhibition of tissue lipid peroxidation, for example in the kidney and heart and more especially in the brain and spinal cords as well as display a detoxifying activity in acute intoxications associated with the peroxidation of lipids of brain tissues such as the brain or spinal cord.

They may be used also in the treatment of biological disorders following trauma. Trauma is understood to mean tissue damage in which the generation of lipid peroxides is involved, and which may be produced by a variety of agents, for example physical agents such as contusions, especially cerebral contusions associated or otherwise with local haemorrhage, or chemical agents such as those used in antitumor chemotherapy, for example adriamycin, or such as those used in cancer immunotherapy, for example IL-2 or TNF. They are most especially advantageous in the treatment of cerebral ischaemia, especially in the treatment of cerebral infarction and in the prevention of its recurrence, or in the treatment of drug intoxication produced by chemotherapy or immunotherapy or a combination of the two.

The novel method of the invention for the treatment of inflammation in warm-blooded animals, including humans, comprises administering to warm-blooded animals an anti-inflammatorily effective amount of at least one compound of formula I and its non-toxic, pharmaceutically acceptable acid addition salts. The compounds may be administered orally or parenterally such as by intra-muscular, intra-articular or intrathecal injection, and preferably by intravenous injection in a bolus or in continuous perfusion, or locally by topical application to the skin or the mucosae. The usual daily dose is 0,02 to 100 mg/kg depending on the condition treated, the specific compound and the method of administration, and preferably 0,01 to 1 mg/kg when administered intravenously or intra-muscularly and optionally several times per day administered.

The compounds of formula II used as starting materials are halogenated derivatives of 3-keto steroids which are new products. Among the preferred new products of formula II are 17α-(3-bromo-1-propynyl)-Δ$^{4,6}$-androstadien-11β,17β-diol-3-one and 17α-(3-bromo-1-propynyl)-6-methyl-Δ$^{1,4,6}$-androstatrien-11β,17β-diol 3-one.

Generally speaking, the compounds of formula II may be prepared according to the following scheme: In the process described in Patent Application No. FR 2,433,536, the lithium derivative of the product of formula.

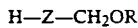

H—Z—CH$_2$OR　　　　　　　　　　　　　　IV in which Z has the above meaning and R is a group protecting the alcohol function is reacted with a steroid of the formula

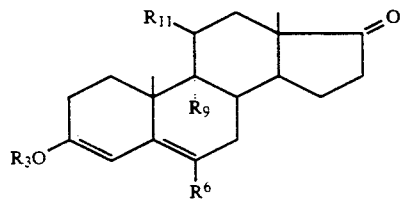

in which $R_6$, $R_9$ and $R_{11}$ have the above meaning and in which $R_3$ is alkyl of 1 to 4 carbon atoms to obtain a product of the formula

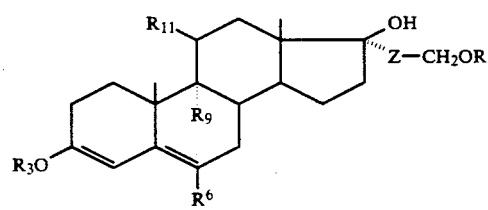

which either is subjected to an agent capable of liberating the ketone function and of creating the-Δ$^{4,6}$-bond system, for example chloranil or 2,3-dichloro-5,6-dicyanobenzoquinone (DDQ) to obtain a product of the formula

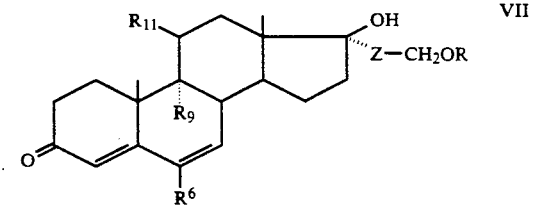

or the ketone function at position 3 is unblocked by acid hydrolysis and then, if desired, the 3-keto-Δ$^4$-product is subjected to an agent for forming the double bond at position 1(2) such as a microorganism like Arthrobacter simplex, or alternatively a stoichiometric amount of DDQ, and then, if desired, to a second stoichiometric amount of DDQ to obtain a further bond at 6(7) position and the alcohol function is then unblocked by acid hydrolysis to obtain the product of the formula

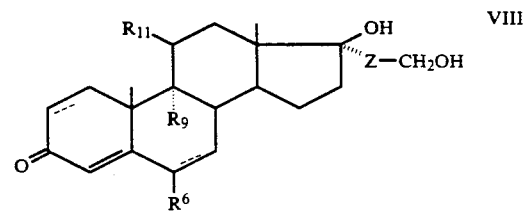

which, if desired, when Z is alkynylene or alkenylene, is subjected to an agent for partial or total hydrogenation, for example using hydrogen in the presence of palladium on active charcoal or on barium sulfate in the presence or absence of triethylamine to obtain the corresponding products having an alkenylene or alkylene Z, and which is subjected to a halogenating agent such as a halide like carbon tetrabromide to obtain a product of a formula corresponding to a product of formula II in which $R_{17}$ is hydrogen. The products obtained may then be subjected, if desired, to an esterifying agent, for example according to the process described in Patent Application No. FR 2,433,536, which introduces the acyl radical at the 17-position only.

The products of formula V necessary for carrying out the process are 17-keto steroids which are known products described, for example, in U.S. Pat. Nos. 2,775,602; 2,793,218; 4,189,431; 3,505,365 or 2,656,370. Steroids of formula V having a double bond at 9(11) position are known products or products prepared by methods known to those skilled in the art, for example by dehydration of a corresponding 11-hydroxylated steroid with a mixture of methane sulfonyl chloride and thionyl chloride.

Steroids of formula V having a 6 methyl are prepared by methods known to those skilled in the art, for example by the action of a methyl magnesium halide on a corresponding 5(6)-epoxy steroid having a ketone at position 3 blocked, for example, by an acetal group.

Steroids of formula V having a 6-fluorine are prepared by known methods, for example by addition of the hydrofluoric acid/dimethylformamide complex to a corresponding 5(6)-epoxy steroid having a ketone at position 3 blocked, for example, by an acetal group.

Steroids of formula V having a 6-chlorine are prepared by known methods, for example by addition of gaseous hydrochloric acid dissolved in acetic acid to a corresponding 5(6)-epoxy steroid having a ketone at position 3 blocked by an acetal group. Steroids of formula V having a 9-fluorine are known products or products prepared by known methods, for example by addition of the hydrofluoric acid/dimethylformamide complex to a corresponding 9(11)-epoxy steroid having a ketone at position 3 blocked, where appropriate, for example, by an acetal group.

The compounds of formula III, used as starting materials for the process of the invention, in which P is unsubstituted or monosubstituted, are prepared according to Patent Application No. WO 87/01,706 as well as the compounds of formula III in which P is disubstituted such as with 2,6-(disubstituted)-4-pyrimidinyl radical, for example a 2,6-bis(1-pyrrolidinyl)-4-pyrimidinyl:

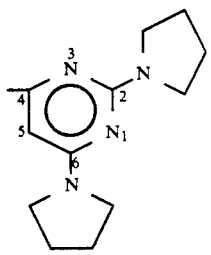

or a 5,6-(disubstituted)-2-pyridyl, for example a 5,6-bis(-diethylamino)-2-pyridyl:

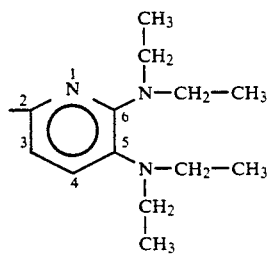

In contrast, the compounds of formula III in which P is a 3,6-(disubstituted)-2-pyridyl, for example a 3,6-bis(-diethylamino)-2-pyridyl

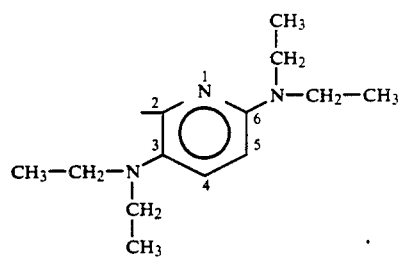

are new products which are prepared as described in French Patent Application No. 89/03740 according to a procedure of which an example of preparation is given later in the experimental part.

The compounds of formula III may be prepared according to the following scheme: a product of the formula

IX in which R' is a group protecting the amino function, for example acetyl, is reacted with a product of the formula

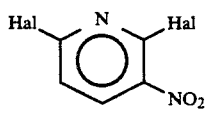

X in which Hal is halogen, preferably chlorine, to obtain a product of the formula

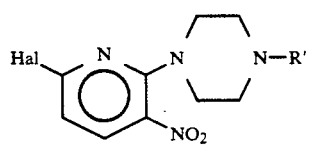

XI which is reacted with a product of the formula

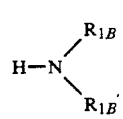

XII in which $R_{1B}$ and $R_{1B'}$ either have the above meaning for $R_B$ and $R_B$ or are such that either one is monovalent group protecting the amino function, for example benzyl or trityl and the other is hydrogen, or $R_{1B}$ and $R_{1B'}$ together represent a divalent protective group, for example $R_{1B}$ and $R_{1B}$ together with the nitrogen to which they are attached, form 2,5-dimethylpyrrole, to obtain a product of the formula

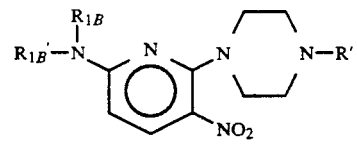

XIII which is subjected to a hydrogenation reaction to obtain a product of the formula

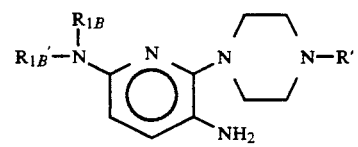

XIV which product, if desired, is: either a) subjected to the action of one or two equivalents of a monohalogenated derivative of $R_A$ or of $R_{A'}$ to obtain a product of the formula

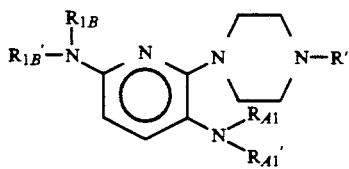
XIV' in which either one of $R_{A1}$ and $R_{A1'}$ is hydrogen and the other alkyl, or both are the same alkyl, or b) subjected to the action of a monohalogenated derivative of $R_A$ or $R_{A'}$ and then to the action of a monohalogenated derivative of $R_{A'}$ or of $R_A$, to obtain a product of the formula

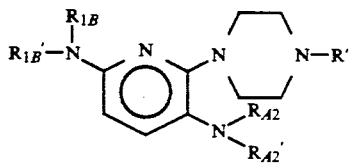
XIV'' in which $R_{A2}$ and $R_{A2'}$ are different alkyl or c) subjected to the action of a dihalogenated derivative of butane or of pentane optionally substituted with alkyl of 1 to 3 carbon atoms to obtain a product of the formula

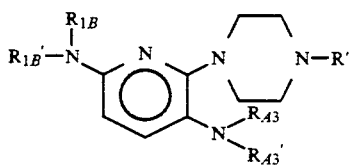
XIV''' in which $R_{A3}$ and $R_{A3'}$ with the atom to which they are attached, form a 5- or 6-membered heterocycle, which products of formulae XIV, XIV', XIV'' and XIV''' are subjected to a reaction of unblocking of the R' and, where appropriate, of $R_{1B}$ and/or $R_{1B'}$ to obtain the corresponding compounds of the formula III.

Among the preferred new products of formula III of the invention are N,N,N',N'-tetraethyl-6-(1-piperazinyl)-2,5-pyridinediamine which, as stated above cannot be obtained according to the preparation described in Patent Application No. WO 87/01,706 and N,N'-dipyrrolidyl-6-(1-piperaziny)-2,5-pyridinediamine.

In the following examples there are described several preferred embodiments to illustrate the invention. However, it is to be understood that the invention is not intended to be limited to the specific embodiments.

PREPARATION 1

17α-(3-bromo-1-propynyl)-Δ$^{4,6}$-androstadien-11β,17β-diol-3-one

STEP A:

3-ethoxy-17α-(3-tetrahydropyranyloxy-1-propynyl)-Δ$^{3,5}$-androstadiene-11β,17β-diol A solution of 4.27 g of tetrahydro-2-(2-propynyloxy)-2H-pyran in 13 ml of ethyl ether was added with stirring to 17.2 ml of a 1.6M solution cooled to −5° to −7° C. of methyllithium in ether and after 30 minutes of stirring at −5° C. to −7° C., a solution of 2.03 g of 3-ethoxy-Δ$^{3,5}$-androstadien-11β-ol-17-one (prepared according to Japanese Patent No. 9577/71) in 14 ml of tetrahydrofuran was added over 1 hour. The mixture was allowed to return to room temperature and was stirred for 4 hours and cooled. 20 ml of saturated aqueous ammonium chloride solution were added and the product was extracted with ethyl acetate. The organic phase was concentrated to dryness under reduced pressure to obtain 5.5 g of crude product which was chromatographed on silica (eluent: cyclohexane/ethyl acetate (6:4)) to obtain 1.57 g of expected product.

IR Spectrum: (CHCl$_3$):

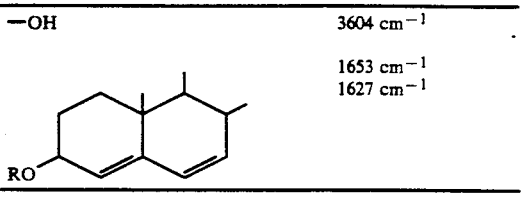

| —OH | 3604 cm$^{-1}$ |
|---|---|
| | 1653 cm$^{-1}$ |
| | 1627 cm$^{-1}$ |

STEP B:

17α-(3-tetrahydropyranyloxy-1-propynyl)-Δ$^{4,6}$-androstadien-11β,17β-diol-3-one 8.2 g of chloranil were added to a solution of 8.2 g of the product of Step A in 164 ml of acetone containing 5% of water, and the mixture was stirred for 4 hours at room temperature. The reaction mixture was poured into 400 ml of a mixture of equal parts of potassium bicarbonate in saturated aqueous solution and 10% strength sodium thiosulfate in water. The product was extracted with methylene chloride and the organic phase was concentrated to dryness under reduced pressure to obtain 8.6 g of crude product which was chromatographed on silica (eluent: cyclohexane/ethyl acetate (4:6)) to obtain 6.65 g of the desired product.

IR Spectrum: (CHCl$_3$):

| Δ$^{4,6}$-3-one | 1654 cm$^{-1}$ |
|---|---|
| | 1618 cm$^{-1}$ |
| | 1584 cm$^{-1}$ |
| | 878 cm$^{-1}$ |
| OH strong band | 3611 cm$^{-1}$ |

STEP C:

17α-(3-hydroxy-1-propynyl)-Δ$^{4,6}$-androstadien-11β,17β-diol-3-one 44 ml of 2N hydrochloric acid were added to a solution of 8.9 g of the product of Step B in 178 ml of ethanol, and the mixture was stirred for 90 minutes at room temperature. It was cooled and 10 ml of concentrated ammonia solution were added. The ethanol was distilled off under reduced pressure and the product was extracted with ethyl acetate. The organic phase was evaporated to dryness under reduced pressure and the 7.89 g of residue were chromatographed on silica (eluent: ethyl acetate/cyclohexane (9:1)) to obtain 6.16 g of crude product. The product was purified by being made into a paste in 10 vol. of isopropyl ether to obtain 5.94 g of the desired product melting at 218° C.

Analysis for C$_{22}$H$_{28}$O$_4$: Calculated: % C 74.12; % H 791; Found: 73.8; 8.0.

IR Spectrum: (CHCl$_3$):

| Δ$^{4,6}$-3-one | 1655 cm$^{-1}$ (S) |
|---|---|
| | 1608 cm$^{-1}$ |

| | |
|---|---|
| | 1584 cm$^{-1}$ |
| | 878 cm$^{-1}$ |
| OH | 3611 cm$^{-1}$ (S) |

STEP D:
17α-(3-bromo-1-propynyl)-Δ$^{4,6}$-androstadien-11β,17β-diol-3-one 6.96 g of carbon tetrabromide were added to a solution of 5 g of the product of Step C in 75 ml of methylene chloride and a solution of 5.5 g of triphenyl-phosphine in 27 ml of methylene chloride was added slowly at $-5°$ C. The mixture was stirred for 30 minutes while the temperature was allowed to return to $+5°$ C., and the reaction medium was chromatographed on silica (eluent: cyclohexane/ethyl acetate (1:1)) to obtain 9.92 g of the product which was chromatographed again on silica (eluent: methylene chloride/methanol (95:5)) to obtain 5.43 g of the desired product melting at 210° C. after crystallization from a methylene chloride/isopropyl ether mixture.

Analysis: $C_{22}H_{27}O_3Br$: Calculated: % C 63.0; % H 6.49; % Br 19.05; Found: 62.8; 6.5; 19.0.

IR Spectrum: (CHCl$_3$):

| | |
|---|---|
| Δ$^{4,6}$-3-one | 1654 cm$^{-1}$ |
| | 1618 cm$^{-1}$ |
| | 1584 cm$^{-1}$ |
| | 878 cm$^{-1}$ |
| OH | 3611 cm$^{-1}$ |

PREPARATION 2
17α-(3-bromo-1-propynyl)-6-methyl-Δ$^{1,4,6}$-androstatrien-11β,17β-diol-3-one

STEP A:
17α-(3-tetrahydropyranyloxy-1-propynyl)-3-ethoxy-6-methyl-Δ$^{3,5}$-androstadiene-11β,17β-diol A solution of 45.75 g of tetrahydro-2-(2-propynyloxy)-2H-pyran in 13 ml of ether was added over 40 minutes to 183 ml of a 1.6M solution cooled to $-5°$ to $-7°$ C. of methyllithium in ether. The mixture was stirred for 30 minutes at $-5°$ to $-7°$ C. and a solution of 22.5 g of 3-ethoxy-6-methyl-Δ$^{3,5}$-androstadien-11β-ol-17-one (prepared according to French Patent Application No. 2,430,952) in 157 ml of tetrahydrofuran was then added over 50 minutes and the mixture was stirred for 15 hours at room temperature. Saturated ammonium chloride solution was added at 0°/+5° C. and after settling was allowed to take place, the product was extracted with ethyl acetate. The organic phase was concentrated to dryness under reduced pressure to obtain 70 g of product which was chromatographed on silica. Elution successively with cyclohexane/ethyl acetate (8:2, 7:3, 6:4, 5:5) (triethylamine 1 part per thousand) yielded 22.6 g of the product which was used for the next step without further treatment.

STEP B:
17α-(3-hydroxy-1-propynyl)-6-methyl-Δ$^{1,4,6}$-androstatrien-11β,17β-diol-3-one a) Oxydation

A solution of 22.6 g of the product of Step A in 406 ml of toluene was added over 5 minutes at 20° C. to 22° C. to a mixture of 37.7 g of dichlorodicyanohydroquinone and 867 ml of toluene. After 1 hour's stirring, the reaction mixture was poured into 1 liter of saturated aqueous sodium bicarbonate solution and the organic phase was separated after settling had taken place and was washed with water saturated with sodium bicarbonate and then with 15% strength aqueous sodium thiosulfate solution. The organic phase was concentrated to dryness under reduced pressure to obtain 19.2 g of 3-keto-Δ$^{1,4,6}$-triene intermediate.

b) Hydrolysis

The said product was stirred for 2 hours at room temperature in 288 ml of methanol and 96 ml of ice-cold 2N hydrochloric acid, and 150 ml of saturated sodium bicarbonate solution were then added slowly. The product was extracted with ethyl acetate and the organic phase was evaporated to dryness. The 16.3 g of residue were chromatographed on silica (eluent: methylene chloride/methanol (8:2)) to obtain 12.63 g of the desired product which was used for the next step without further treatment. 1.740 g of the product were crystallized from methylene chloride and then crystallized from ethyl acetate to obtain 1.36 g of pure product melting at 175° C. and having a specific rotation of $[α]_D = -93.5° \pm 3°$ C. (C=0.5% in ethanol).

Analysis $C_{23}H_{28}O_4$: Calculated: % C 74.97; % H 7.65; Found: 75.2; 7.8.

IR Spectrum (CHCl$_3$):

| | |
|---|---|
| Conjugated ketone | 1647 cm$^{-1}$ |
| | 1596 cm$^{-1}$ |
| | 891 cm$^{-1}$ |
| Free OH | 3609 cm$^{-1}$ |

STEP C:
17α-(3-bromo-1-propynyl)-6-methyl-Δ$^{1,4,6}$-androstatrien-11β,17β-diol-3-one Using the procedure of Step D of Preparation 1, 10 g of the product of Step B were reacted to obtain 8.813 g of the desired product. 1.83 g of the product were chromatographed again on silica (eluent: ethyl acetate/cyclohexane (8:2)) to obtain 794 mg of the product having a specific rotation of $[α]_D = -93.5° \pm 3°$ (C=0.5% in ethanol)

Analysis: $C_{23}H_{27}O_3Br$: Calculated: % C 63.26; % H 6.53; % Br 17.03; Found: 63.4; 6.7; 17.4.

IR Spectrum: (CHCl$_3$):

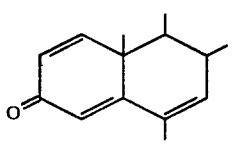

| | |
|---|---|
| | 1651 cm$^{-1}$ |
| | 1607 cm$^{-1}$ Max |
| | 1584 cm$^{-1}$ Should. |
| | 891 cm$^{-1}$ |
| OH | 3611 cm$^{-1}$ (+ associated) |

PREPARATION 3

N,N,N',N'-tetraethyl-6-(1-piperazinyl)-2,5-pyridinediamine

STEP A:

1-acetyl-4-[6-(diethylamino)-3-nitro-2-pyridyl]-piperazine

A solution of 51.22 g of N-acetylpiperazine in 200 ml of acetonitrile was added over 50 minutes at 0° C. to a mixture of 78 g of 2,6-dichloro-3-nitropyridine, 600 ml of acetonitrile and 66.3 g of potassium carbonate. The mixture was allowed to return to room temperature and was stirred for 75 minutes. The inorganic salts were filtered off and after 180 ml of N,N-diethylamine and 76 g of potassium carbonate were added to the filtrate, the mixture was refluxed for 75 minutes. The inorganic salts were filtered off after cooling and the filtrate was evaporated to dryness under reduced pressure. The 166.9 g of residue were crystallized from 200 ml of ethyl acetate to obtain 87.4 g of the expected product melting at 120° C.

IR Spectrum: (CHCl$_3$):

| | |
|---|---|
| $\rangle$=O 1637 cm$^{-1}$ | 1637 cm$^{-1}$ |
| Conjugated system | 1593 cm$^{-1}$ |
| 1st NO$_2$ band | 1569 cm$^{-1}$ − 1510 cm$^{-1}$ |
| 2nd NO$_2$ band | 1346 or 1299 cm$^{-1}$ |

STEP B:

N,N,N',N'-tetraethyl-6-(1-piperazinyl)-2,5-pyridinediamine

A mixture of 70 g of the product of Step A, 1500 ml of methanol, 61.5 ml of acetaldehyde and 10 g of activated charcoal containing 10% of palladium was hydrogenated at a maximum pressure of 1250 mbar of mercury at 25° C. Approximately 20 liters of hydrogen were absorbed and then the catalyst was filtered off and the filtrate was evaporated to dryness under reduced pressure. The 89.8 g of residue were taken up in 500 ml of n-propanol and 91.3 g of potassium hydroxide pellets and the mixture was refluxed for 3 hours. The cooled solution was poured into 1 liter of ice-cold water and the mixture was extracted with methylene chloride. The organic solution was washed with saturated sodium chloride solution, dried, filtered and concentrated to dryness under reduced pressure. The 58.9 g of residue were chromatographed on silica (eluent: methylene chloride/methanol/ammonia solution (95:5:0.5)) to obtain 48.35 g of the expected product which was used without further treatment.

Analysis C$_{17}$H$_{31}$N$_5$: Calculated: % C 66.84; % H 10.23; % N 22.93; Found: 66.9; 10.5; 22.6.

IR Spectrum (CHCl$_3$):

| | |
|---|---|
| C = C | 1596 cm$^{-1}$ |
| C = N | 1560 cm$^{-1}$ |
| Heteroaromatic | 1531 cm$^{-1}$ |
| | 1487 cm$^{-1}$ |

EXAMPLE 1

17α-[3-{4-[(2,6-bis(1-pyrrolidinyl)-4-pyrimidinyl]-1-piperazinyl}-1-propynyl]-Δ$^{4,6}$-androstadien-11β,17β-diol-3-one methanesulfonate 6.834 g of 2,4-bis(1-pyrrolidinyl)-6-(1-piperazinyl)-pyrimidine (prepared in Patent No. WO 87/01,706 and 3.180 g of potassium carbonate were added to a solution of 4.741 g of the product of Step D of Preparation 1. The mixture was stirred for 1 hour, the insoluble matter was then filtered off and the mixture was concentrated to dryness under reduced pressure. The residue was chromatographed on silica (eluent: methylene chloride/methanol/ammonia solution (95:5:0.5)) to obtain 6.52 g of product which was dissolved in 500 ml of methylene chloride. The insoluble matter was filtered off, 100 ml of isopropanol were added and the methylene chloride was evaporated off. The suspension was chilled to 0° C. and drained to obtain 5.66 g of the free base melting at 266° C.

Salification 1 g of the said base was dissolved in 600 ml of methanol and 10.4 ml of a 0.3M solution of methanesulfonic acid in ethyl acetate were added. The mixture was concentrated under reduced pressure to 100 ml, the methanol being replaced by the addition of ethyl acetate during the distillation. The salt crystallized from ethyl acetate at 0° C. was drained to obtain 1.163 g of the desired product melting at 225° C. (somewhat indistinct).

Analysis C$_{38}$H$_{52}$O$_3$N$_6$. 2CH$_3$SO$_3$H: Calculated: % C 57.66; % H 7.25; % N 10.08; % S 7.69; Found: 57.35; 7.3; 9.9; 7.7.

IR Spectrum (CHCl$_3$):

| | |
|---|---|
| OH | 3610 cm$^{-1}$ (+ associated) |
| Δ$^{4,6}$-3-one | 1654 cm$^{-1}$ |
| | 1617 cm$^{-1}$ |
| | 878 cm$^{-1}$ |
| Conjugated system of the copula | 1559 cm$^{-1}$ (S) |
| | 1552 cm$^{-1}$ (S) |
| | 1487 cm$^{-1}$ (S) |

EXAMPLE 2

17α-[3-{4-[(2-,6-bis(1-pyrrolidinyl)-4-pyrimidinyl]-1-piperazinyl}-1-propynyl]-6-methyl-Δ$^{1,4,6}$-androstatrien-11,17-diol-3-one A mixture of 1.509 g of the product of Step C of Preparation 2 in 22 ml of acetone, 2.116 g of 2,4-bis(1-pyrrolidinyl)-6-(1-piperazinyl)-pyrimidine (prepared in Patent No. WO 87/01,706 and 0.986 g of potassium carbonate was stirred for 3 hours 45 minutes at room temperature. The insoluble matter was filtered off, washed with acetone and then with methylene chloride containing 5% of methanol. The filtrate was evaporated to dryness and the residue was chromatographed on silica (eluent: methylene chloride/methanol (95:5)) to obtain 1.872 g of the crude expected product. 741 mg of a previous preparation were added to the product obtained above and the mixture was chromatographed on silica (eluent: ethyl acetate/methanol (95:5)). The 2.331 g of collected dry extract were crystallized in 10 ml of ethyl acetate to obtain 2.2 g of the desired product melting at ≈275° C.

Analysis C₃₉H₅₂O₃N₆: Calculated: % C 71.74; % H 8.02; % N 12.87; Found: 71.7; 8.2; 12.5.
IR Spectrum: (CHCl₃):

| OH | 3609 cm⁻¹ |
|---|---|
| | 1651 cm⁻¹ |
| | 1607 cm⁻¹ |
| | 891 cm⁻¹ |
| Conjugated system | 1564 cm⁻¹ (S. Max.) |
| | 1554 cm⁻¹ (Should.) |
| | 1522 cm⁻¹ (Should.) |
| | 1487 cm⁻¹ (Should.) |

EXAMPLE 3

17α-[3-{4-[5,6-bis(diethylamino)-2-pyridyl]-1-piperazinyl}-1-propynyl]-6-methyl-Δ$^{1,4,6}$-androstatrien-11β,17β-diol-3-one Using the procedure of Example 2, 2 g of the product of Step C of Preparation 2 and 2.828 g of N,N,N',N'-tetraethyl-6-(1-piperazinyl)-2,3-pyridinediamine (prepared according to Patent No. WO 87/01,706 were reacted to obtain 4.684 g of crude product which was chromatographed on silica (eluent: methylene chloride/methanol (95:5), then ethyl acetate/methanol (95:5)) to obtain 2.65 g of the desired product with a specific rotation of $[\alpha]_D = -72.5° \pm 2.5°$ (C=0.5% in ethanol).

Analysis: C₄₀H₅₇O₃N₅: Calculated: % C 72.43; % H 8.77; % N 10.22; Found: 72.3; 8.8; 10.1.

IR Spectrum (CHCl₃):

| OH | 3611 cm⁻¹ |
|---|---|
| Conjugated ketone | 1651 cm⁻¹ |
| | 1607 cm⁻¹ Type |
| | 891 cm⁻¹ |
| Conjugated system | 1586 cm⁻¹ |
| | 1565 cm⁻¹ |
| | 1477 cm⁻¹ |
| | 1732 cm⁻¹ |

EXAMPLE 4

17α-[3-{4-[3,6-bis(diethylamino)-2-pyridyl]-1-piperazinyl}-1-propynyl]-6-methyl-Δ$^{1,4,6}$-androstatrien-11β,17β-diol-3-one Using the procedure of Example 3, 2 g of the product of Step C of Preparation 2 and 2.83 g of N,N,N',N'-tetraethyl-6-(1-piperazinyl)-2,5-pyridinediamine (prepared according to French Patent Application No. 89/03740 and obtained according to Step B of Preparation 3) were reacted to obtain 1.75 g of the expected product which was chromatographed a 3rd time on silica (eluent: ethyl acetate/methanol (96:4)) to obtain 1.458 g of the desired product with a specific rotation of $[\alpha]_D = -83.5° \pm 2.5°$ (C=0.5% in ethanol).

Analysis: C₄₀H₅₇O₃N₅: Calculated: % C 72.8; % H 8.76; % N 10.43; Found: 72.6; 8.8; 10.4.

IR Spectrum (CHCl₃):

| OH | 3611 cm⁻¹ |
|---|---|
| | 1651 cm⁻¹ |
| | 1606 cm⁻¹ |
| | 891 cm⁻¹ |
| Conjugated system | 1595 cm⁻¹ |
| | 1561 cm⁻¹ |
| | 1486 cm⁻¹ |

PHARMACOLOGICAL STUDY

A. Antioxidant activity

The antioxidant activity was tested for in vitro by the test of formation of malondialdehyde (MDA) which measures lipid peroxidation triggered: either a) non-enzymatically by ferrous sulfate, in 1) brain homogenates, or 2) rat liver microsomes or b) enzymatically by NADPH and carbon tetrachloride in rat liver microsomes.

1.1 MDA formation was measured on 10-fold diluted (V/V) homogenates of brains of S-D rats (200 g) prepared in Krebs buffer pH 7.4 under the conditions described in J. Biol. Chem., Vol. 262 (1987), p. 10438 to 10440. 1 ml of homogenate was incubated for 60 minutes at 37° C. in the presence of 25 microliters of ethanol or water or a mixture of the two depending on the product containing or not containing the test product, after the addition of 25 microliters of ferrous sulfate solution prepared immediately before use in water outgassed with argon (200 micromoles final). 0.25 ml of incubated mixture were withdrawn and 1.5 ml of 1% strength phosphoric acid, 0.25 ml of a solution containing 200 micromoles of deferoxamine (Desferal$^\phi$, Ciba Geigy) in water, 10 microliters of butylated hydroxytoluene (BHT) at a concentration of 8.7 mg/ml in ethanol and 0.5 ml of thiobarbituric acid (TBA) at a concentration of 0.6% in water were added. The mixture was heated to 100° C. for 45 minutes and cooled. 4 ml of n-butanol were added and the mixture was centrifuged for 15 minutes at 4000 rpm and the OD of the supernatant fraction was then read at 535 nm. The reaction blanks in the absence of Fe$^{++}$ were incubated under the same conditions. The percentage inhibition was calculated:

$$\text{percentage inhibition} = \frac{\text{OD in the presence of product}}{\text{OD in the absence of product}}$$

| | percentage inhibition | | |
|---|---|---|---|
| Concentration | $5 * 10^{-4}$M | $1 * 10^{-4}$M | $1 * 10^{-5}$M |
| test product | | | |
| product of Example 1 | 60.8 ± 3.0 | 9.8 ± 11.2 | −10.6 ± 9.0 |
| product of Example 2 | 53.1 ± 7.8 | 26.6 ± 3.9 | 28.0 ± 4.1 |
| product of Example 3 | 64.2 ± 10 | 62.9 ± 4.5 | 51.3 ± 13.7 |
| product of | 65.4 ± 10.1 | 51.0 ± 12.4 | 48.5 ± 13.1 |

-continued $$\text{percentage inhibition} = \frac{\text{OD in the presence of product}}{\text{OD in the absence of product}}$$

| | percentage inhibition | | |
|---|---|---|---|
| Concentration | $5*10^{-4}M$ | $1*10^{-4}M$ | $1*10^{-5}M$ |
| Example 4 | | | |

1.2: MDA formation was measured on liver microsomes of S-D rats (200 g) prepared from the fraction sedimented at 100,000 g of a liver homogenate in a sucrose buffer of which the fraction remaining insoluble at 100,000 g in 100 mM sodium pyrophosphate buffer pH 7.4 was used and which was homogenized in 100 mM sodium phosphate buffer pH 7.4 containing 20% of glycerol and was then stored at −80° C.

The microsomes were incubated for 15 minutes at 37° C. in 1 ml containing 35 mM Tris-HCl buffer/0.1M KCl pH 7.4, 1 mg of microsomal protein, 5 microliters of ethanol containing or not containing the test product and 250 microliters of ascorbate solution in the Tris buffer (0.5 mM final), after the addition of 250 microliters of ferrous sulfate prepared immediately before use in the Tris buffer (6 micromoles final). The reaction was stopped by adding 2 ml of a 1M solution of trichloroacetic acid in 0.25M hydrochloric acid containing 0.4% of thiobarbituric acid. The mixture was heated to 85° C. for 25 minutes, cooled and centrifuged for 15 minutes at 3500 rpm, and the OD of the supernatant fraction was then read at 535 nm. The reaction blanks in the absence of Fe++ were performed at the same time. The percentage inhibition was calculated as above.

| | concentration | | | |
|---|---|---|---|---|
| test product | $5*10^{-5}M$ | $1*10^{-5}M$ | $5*10^{-6}M$ | $1*10^{-6}M$ |
| | percentage inhibition | | | |
| product of Example 1 | 97.5 ± 0.5 | 46 ± 3 | 19.5 ± 6 | 0 ± 18 |
| product of Example 2 | 85 ± 1.5 | 11.3 ± 2 | 0 ± 3 | 0 ± 2 |
| product of Example 3 | | 95.5 | 99.5 | 55 ± 9 |
| product of Example 4 | | 100 | 99.5 | 51 ± 3 |

2: MDA formation was measured on liver microsomes of rats pretreated with phenobarbital (80 mg/kg by daily intraperitoneal injection for 4 days), prepared as described above. The microsomes were incubated for 15 minutes at 37° C. in 1 ml containing 0.1M phosphate buffer, pH 7.4 phosphate buffer, 1 mg of microsomal protein, 5 microliters of ethanol containing or not containing the test product and 5 microliters of carbon tetrachloride (5.5 mM final) after the addition of 50 microliters of NADPH solution in the phosphate buffer (1 mM final). The reaction was stopped and the assay was then performed according to the conditions described above.

| | concentration | | |
|---|---|---|---|
| test product | $1*10^{-5}M$ | $5*10^{-6}M$ | $1*10^{-6}M$ |
| | percentage inhibition | | |
| product of Example 1 | 86 ± 2 | 75 ± 4 | 16 ± 1 |
| product of Example 2 | 80 ± 1 | 61 ± 1.5 | 22 ± 1.5 |
| product of Example 3 | 93 | 89 ± 2 | 48 ± 2 |

| | concentration | | |
|---|---|---|---|
| test product | $1*10^{-5}M$ | $5*10^{-6}M$ | $1*10^{-6}M$ |
| | percentage inhibition | | |
| product of Example 4 | 91 ± 2 | 85 | 49 ± 2 |

Various modifications of the products and method of the invention may be made without departing from the spirit or scope thereof and it is to be understood that the invention is intended to be limited only as defined in the appended claims.

What we claim is:

1. A compound selected from the group consisting of a compound of the formula

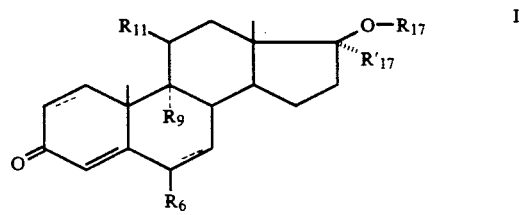

wherein $R_6$ is selected from the group consisting of hydrogen, —$CH_3$, fluorine and chlorine, $R_9$ and $R_{11}$ together form a second bond at 9(11) or $R_9$ is hydrogen or fluorine and $R_{11}$ is selected from the group consisting of hydrogen, OH and =O the dotted lines in rings A and B indicate the possible additional bond at 1(2) and 6(7), $R_{17}$ is hydrogen or acyl of an carboxylic acid of 1 to 18 carbon atoms, $R'_{17}$ is

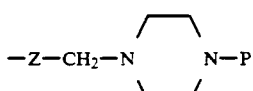

Z is alkynylene of 2 to 5 carbon atoms, P is pyrimidinyl or pyridyl optionally substituted with one or two individual members of the group consisting of —$NH_2$, alkylamino, dialkylamino and pyrolidine, piperidine and pyrrole optionally substituted on the nitrogen with alkyl of 1 to 3 carbon atoms and its non-toxic, pharmaceutically acceptable acid addition salts.

2. A compound of claim 1 wherein P is pyrimidyl or pyridyl substituted with two individual members of the group consisting of dialkylamino and pyrolidine, piperidine and pyrrole.

3. A compound of claim 1 wherein P is 2,6-bis(1-pyrrolidinyl)-4-pyrimidinyl or 5,6-bis(diethylamino)-2-pyridyl or 3,6-bis(diethylamino)-2-pyridyl.

4. A compound of claim 1 wherein $R_6$ is hydrogen.

5. A compound of claim 1 wherein $R_6$ is —$CH_3$.

6. A compound of claim 1 wherein the 6(7) dotted line is a second bond.

7. A compound of claim 1 wherein $R_9$ is hydrogen and $R_{11}$ is —OH.

8. A compound of claim 1 wherein the 1(2) dotted line is a second bond.

9. A compound of claim 1 wherein $R_{17}$ is hydrogen.

10. A compound of claim 1 wherein $R'_{17}$ is

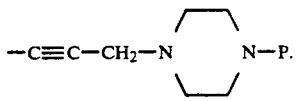

11. A compound of claim 1 selected from the group consisting of 17α-[3-{4-[2,6-bis(1-pyrrolidinyl)-4-pyrimidinyl]-1-piperazinyl}-1-propynyl]-Δ⁴,⁶-androstadien-11β,17β-diol-3-one, 17α-[3-{4-[2,6-bis(1-pyrrolidinyl)-4-pyrimidinyl]-1-piperazinyl}-1-propynyl]-6-methyl-Δ¹,⁴,⁶-androstatrien-11β,17β-diol-3-one, 17α-[3-{4-[5,6-bis(diethylamino)-2-pyridyl]-1-piperazinyl}-1-propynyl]-6-methyl-Δ¹,⁴,⁶-androstatrien-11β,17β-diol-3-one, 17α-[3-{4-[3,6-bis(diethylamino)-2-pyridyl]-1-piperazinyl}-1-propynyl]-6-methyl-Δ¹,⁴,⁶-androstatrien-11β,17β-diol-3-one and their non-toxic, pharmaceutically acceptable acid addition salts.

12. A compound of the formula

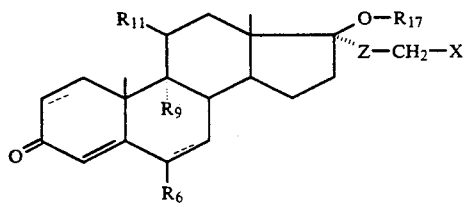

wherein $R_6$, $R_9$, $R_{11}$, $R_{17}$, Z and the dotted lines have the definitions of claim 1 and X is halogen.

13. A compound of claim 12 selected from the group consisting of 17α-(3-bromo-1-propynyl)-Δ⁴,⁶-androstadien-11β,17β-diol-3-one and 17α-(3-bromo-1-propynyl)-6-methyl-Δ¹,⁴,⁶-androstatrien-11β,17β-diol-3-one.

14. An anti-oxidant composition comprising an anti-oxidantically effective amount of at least one compound of claim 1 and an inert pharmaceutical carrier.

15. A composition of claim 14 wherein P is pyrimidyl or pyridyl substituted with two individual members of the group consisting of dialkylamino and pyrolidine, piperidine and pyrrole.

16. A composition of claim 14 wherein P is 2,6-bis(1-pyrrolidinyl)-4-pyrimidinyl or 5,6-bis(diethylamino)-2-pyridyl or 3,6-bis(diethylamino)-2-pyridyl.

17. A composition of claim 14 wherein $R_6$ is hydrogen.

18. A composition of claim 14 wherein $R_6$ is —$CH_3$.

19. A composition of claim 14 wherein the 6(7) dotted line is a second bond.

20. A composition of claim 14 wherein $R_9$ is hydrogen and $R_{11}$ is —OH.

21. A composition of claim 14 wherein the 1(2) dotted line is a second bond.

22. A composition of claim 14 wherein $R_{17}$ is hydrogen.

23. A composition of claim 14 wherein $R'_{17}$ is

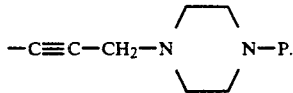

24. A composition of claim 14 wherein the active compound is selected from the group consisting of 17α-[3-4-[2,6-bis(1-pyrrolidinyl)-4-pyrimidinyl]-1-piperazinyl-1-propynyl]-Δ⁴,⁶-androstadien-11β,17β-diol-3-one, 17α-[3-{4-[2,6-bis(1-pyrrolidinyl)-4-pyrimidinyl]-1-piperazinyl}-1-propynyl]-6-methyl-Δ¹,⁴,⁶-androstatrien-11β,17β-diol-3-one, 17α-[3-{4-[5,6-bis(diethylamino)-2-pyridyl]-1-piperazinyl}-1-propynyl]-6-methyl-Δ¹,⁴,⁶-androstatrien-11β,17β-diol-3-one, 17α-[3-{4-[3,6-bis(diethylamino)-2-pyridyl]-1-piperazinyl}-1-propynyl]-6-methyl-Δ¹,⁴,⁶-androstatrien-11β,17β-diol-3-one and their non-toxic, pharmaceutically acceptable acid addition salts.

25. A method of inducing anti-oxidant activity in warm-blooded animals comprising administering to warm-blooded animals an anti-oxidantically effective amount of at least one compound of claim 1.

26. A method of claim 25 wherein P is pyrimidyl or pyridyl substituted with two individual members of the group consisting of dialkylamino and pyrolidine, piperidine and pyrrole.

27. A method of claim 25 wherein P is 2,6-bis(1-pyrrolidinyl)-4-pyrimidinyl or 5,6-bis(diethylamino)-2-pyridyl or 3,6-bis(diethylamino)-2-pyridyl.

28. A method of claim 25 wherein $R_6$ is hydrogen.

29. A method of claim 25 wherein $R_6$ is —$CH_3$.

30. A method of claim 25 wherein the 6(7) dotted line is a second bond.

31. A method of claim 25 wherein $R_9$ is hydrogen and $R_{11}$ is —OH.

32. A method of claim 25 wherein the 1(2) dotted line is a second bond.

33. A method of claim 25 wherein $R_{17}$ is hydrogen.

34. A method of claim 25 wherein $R'_{17}$ is

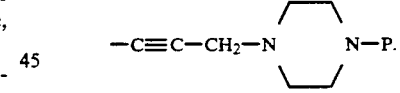

35. A method of claim 25 selected from the group consisting of 17α-[3-{4-[2,6-bis(1-pyrrolidinyl)-4-pyrimidinyl]-1-piperazinyl}-1-propynyl]-Δ⁴,⁶-androstadien-11β,17β-diol-3-one, 17α-[3-{4-[2,6-bis(1-pyrrolidinyl)-4-pyrimidinyl]-1-piperazinyl}-1-propynyl]-6-methyl-Δ¹,⁴,⁶-androstatrien-11β,17β-diol-3-one, 17α-[3-{4-[5,6-bis(diethylamino)-2-pyridyl]-1-piperazinyl}-1-propynyl]-6-methyl-Δ¹,⁴,⁶-androstatrien-11β,17β-diol-3-one, 17α-[3-{4-[3,6-bis(diethylamino)-2-pyridyl]-1-piperazinyl}-1-propynyl]-6-methyl-Δ¹,⁴,⁶-androstatrien-11β,17β-diol-3-one and their non-toxic, pharmaceutically acceptable acid addition salts.

* * * * *